(12) United States Patent
White

(10) Patent No.: US 6,431,861 B1
(45) Date of Patent: Aug. 13, 2002

(54) ORTHODONTIC ARCHWIRE

(75) Inventor: Velton C. White, W. 590 Kearney Rd., Burlington, WI (US) 53105

(73) Assignee: Velton C. White, Burlington, WI (US)

(*) Notice: Subject to any disclaimer, the term of this patent is extended or adjusted under 35 U.S.C. 154(b) by 0 days.

(21) Appl. No.: 09/569,837

(22) Filed: May 11, 2000

Related U.S. Application Data

(60) Provisional application No. 60/133,606, filed on May 11, 1999.

(51) Int. Cl.⁷ .................................................. A61C 3/00

(52) U.S. Cl. .......................................... 433/20; 433/24

(58) Field of Search ........................................ 433/20, 24

(56) References Cited

U.S. PATENT DOCUMENTS

| | | | |
|---|---|---|---|
| 4,268,250 A | 5/1981 | Reeve | 433/20 |
| 4,818,225 A | 4/1989 | Fasnacht | 433/18 |
| 4,818,226 A | 4/1989 | Berendt et al. | 433/20 |
| 5,167,499 A | 12/1992 | Arndt et al. | 433/7 |
| RE35,170 E | 3/1996 | Arndt et al. | 433/7 |
| 5,683,245 A | * 11/1997 | Sachdeva et al. | 433/20 |

OTHER PUBLICATIONS

"Biolastic Superelastic Nickel–Titanium Preformed Arches" Brochure, RMO, Published by end of 1989, 2 Pages.

* cited by examiner

*Primary Examiner*—Todd E. Manahan
(74) *Attorney, Agent, or Firm*—Marsh Fischmann & Breyfogle LLP

(57) ABSTRACT

An inventive orthodontic archwire and method of use is described. The inventive archwire includes a central curved portion and first and second end portions extending from opposing ends of the central curved portion. The central curved portion includes a middle section that arcuately projects one of upwardly and downwardly relative to a reference plane. The central curved portion further includes first and second intermediate sections extending from opposing ends of the middle section, each of said first and second intermediate sections arcuately projecting in an orientation opposite to that of the arcuate middle section. The orthodontic archwire may preferably exhibit a relatively high ultimate tensile strength of between about 275 KSI and 330 KSI. The first and second end portions may extend from the central curved portion so as to lie substantially parallel to or coplanar with the reference plane of the orthodontic archwire and/or substantially non-convergently. The disclosed archwire yields rapid tooth positioning and reduces or substantially avoids undesired attendant tooth movement (e.g. molar tipping, rotation or tooth movement).

35 Claims, 4 Drawing Sheets

ORTHODONTIC ARCHWIRE

RELATED APPLICATION

This application is related to U.S. Provisional Application Ser. No. 60/133,606, filed May 11, 1999, entitled "A VERTICALLY AND HORIZONTALLY ACTING ORTHODONTIC ARCHWIRE", hereby incorporated by reference.

FIELD OF THE INVENTION

The present invention is directed to an improved orthodontic archwire, and more particularly, to a vertically-acting, and optionally horizontally-acting, archwire that provides for rapid tooth positioning and overall enhanced results in orthodontic treatment.

BACKGROUND OF THE INVENTION

Orthodontic archwires are utilized to provide corrective tooth positioning forces in orthodontic treatment programs. For such purposes, archwires may be provided so as apply extrusive and/or intrusive forces to maxillary and/or mandibular bicuspids and/or incisors. Further, archwires may be employed to apply arch widening or narrowing forces.

Typically, the use of orthodontic archwires progresses in a number of phases. In a traditional first phase of treatment one or a succession of relatively flexible wires are utilized to position teeth to a first degree, followed by a second phase in which one or a succession of relatively stiff finishing archwires are employed to obtain a final desired arch form. The flexible wires utilized in phase I treatment may be generally characterized as having a relatively low modulus of elasticity in tension, including for example super elastic nickel titanium archwires, titanium molybdenum archwires and stainless steel woven, twisted or braided archwires. In contrast, phase II archwires may be generally characterized as having a relatively high modulus of elasticity in tension, including in particular monolithic stainless steel archwires arcuately configured to lie within a flat plane or to match a desired curve of spee in a passive state.

Although orthodontic archwires of the above-noted nature have been employed to yield acceptable results, the cumulative time of treatment can be quite extensive and entail a significant number of office visits. Further, depending on the type of orthodontic archwire(s) employed, undesired tooth movement may accompany intrusive/extrusive tooth movement, including in particular undesired molar tipping (e.g., crown tipping to the distal/root tipping to the mesial), molar rotation (e.g., to the distal) and molar root movement (e.g., the buccal).

SUMMARY OF THE INVENTION

In view of the foregoing, a primary objective of the present invention is to provide an orthodontic archwire that effects rapid bicuspid intrusion/extrusion and/or rapid incisor extrusion/intrusion.

An additional objective of the present invention is to address the above-noted objectives, while reducing or substantially avoiding undesired tooth movement, including undesired molar tipping, rotation and/or root movement.

Yet another objective of the present invention is to provide a multi-functional orthodontic archwire that may be utilized to achieve rapid bicuspid and/or incisor intrusion/extrusion as may be desired, while further providing for an increase or decrease of inter-canine and inter-molar distances in the maxillary and/or mandibular as may be desirable on a patient-by-patient basis.

One or more of the above-noted objectives and additional advantages may be realized in an inventive orthodontic archwire that includes a central curved portion and first and second end portions extending from opposing ends o[0086] the central curved portion. The central curved portion includes a middle section and first and second intermediate sections extending from opposing ends of the middle section. In a passive state, the middle section arcuately projects one of upwardly and downwardly with respect to a reference plane (e.g., to define a shallow, upright or downward arc), and the first and second intermediate sections arcuately project oppositely to the middle section with respect to the reference plane (e.g., to define a shallow, downward or upright arc). By way of further descriptive illustration, when the arcuate middle section is oriented upward and the arcuate intermediate sections are oriented downward, a gentle saddle-like configuration is defined by the archwire. As will be further described, the opposite vertical orientations of the arcuate middle and intermediate sections provide for the deflection of such sections into opposite corresponding orientations when the archwire is activated upon installation in a patient's mouth. Such deflective activation provides the necessary vertically-acting, corrective positioning forces to effect bicuspid intrusion/extrusion and/or incisor extrusion/intrusion.

In one aspect of the present invention, the first and second end portions may be provided to extend substantially non-convergently (i.e., relative to each other) from opposing ends of the central curved portion of the archwire in both a passive state and when the archwire is installed. More particularly, in a passive state, the end portions may be provided to extend from opposing ends of the central curved portion within an angle range of between about 0° to ±30° relative to an archwire mid-line (e.g., in a plan view). In a preferred embodiment, the end portions each extend linearly from the central curved portion in a plan view.

In another related aspect of the present invention, the first and second end portions of the inventive archwire may be provided so as to extend from opposing ends of the central curved portion substantially parallel to or substantially within the reference plane of the archwire in both a passive state and when the archwire is installed. More particularly, the first and second end portions may extend from opposing ends of the central curved portion within an angle range of between about ±5° relative to the reference plane (e.g., in a side view). In one embodiment, the end portions each extend substantially linearly within or parallel to the reference plane. As will be appreciated, the reference plane of the archwire is established so that upon installation of the archwire the reference plane will assume a position substantially parallel to a desired occlusal plane.

The provision of end portions configured in accordance with one or more of the noted aspects reduces or substantially avoids the application of undesired forces to interconnected teeth during use of the inventive archwire. As such, undesired tooth movement is reduced or avoided, including, for example, undesired molar tipping, rotation and/or root movement.

In another aspect of the present invention, the arcuate middle section of the orthodontic archwire may be provided so as to have a maximum projection of between about 0.3 mm and 0.6 mm relative to the reference plane in a passive state. Further, the arcuate first and second intermediate sections may be provided to each have a maximum projection of between about 2 mm and 4 mm relative to the reference plane in a passive state.

In a related important aspect of the present invention, the archwire may be provided to have a modulus of elasticity in tension, sometimes referred to as a modulus of stiffness, of between about $2.8 \times 10^6$ and $3.2 \times 10^6$. In a different measure, the archwire may be provided to have an ultimate tensile strength of between about 275 KSI and 330 KSI (i.e., thousand pounds per square inch), and most preferably at least about 310 KSI. Further, the archwire preferably has a round cross-section, with a diameter of between about 0.012" and 0.022". Square, rectangular, woven and braided configurations may also be utilized. By way of example, the archwire may be fabricated from relatively hard, high tensile metal and/or metal alloy comprising chromium, nickel, molybdenum, manganese or iron.

In a further related aspect of the invention, the inventive archwire may be provided so that upon deflected activation when installed the arcuate middle section applies a total force of between about 45 gm to 65 gm per mm of deflection to the interconnected teeth (e.g., 135 gms–195 gms applied for a 3 mm deflection). Similarly, the intermediate sections may be provided so that upon activation they each apply a total force of between about 45 gm to 65 gm per mm deflection to the interconnected teeth.

In an additional aspect of the present invention, a plurality of archwires having one or more of the above-noted features may be provided in varying cross-widths for intended use in the maxillary and/or a plurality of archwires having one or more of the above-noted features may be provided in varying cross-widths for intended mandibular use. The provision of such archwire sets allows for the successive multi-functional use of the archwires to achieve tooth extrusion/intrusion contemporaneous with a desired degree of arch expansion, narrowing or width-maintenance.

In yet an additional aspect of the present invention, the curved portion of the inventive orthodontic archwire may optionally include first and second anterior step-out portions interposed between the arcuate middle section and the arcuate first and second intermediate sections, respectively. The provision of the anterior step-out portions accommodates the buccal offset projection of the cuspids in normal applications.

In a related important aspect of the present invention, the archwire may be provided to have a relatively high modulus of elasticity in tension, sometimes referred to as a modulus of stiffniess. In one measure, the archwire may be provided to have an ultimate tensile strength of between about 275 KSI and 330 KSI (i.e. thousand pounds per square inch), and most preferably at least about 310 KSI. Further, the archwire preferably has a round cross-section, with a diameter of between about 0.012" and 0.022". Square, rectangular, woven and braided configurations may also be utilized. By way of example, the archwire may be fabricated from relatively hard, high tensile metal or metal alloy comprising chromium, cobalt, nickel, molybdenum, manganese or iron (e.g. a chromium-cobalt alloy).

In conjunction with the present invention an inventive method is also disclosed for use of one or more inventive orthodontic archwires. Such inventive method includes the step of first installing a first orthodontic archwire in a patient's mouth, wherein the first orthodontic archwire is deflected from a passive state to an activated state, and wherein the first orthodontic archwire is of a configuration having one or more features as described above. Specifically, the first orthodontic archwire may include first and second end portions extending from opposing ends of a central curved portion, said central curved portion having oppositely oriented middle and first/second intermediate sections which arcuately project from the reference place, and wherein the archwire preferably has an ultimate tensile strength of at least about 310 KSI. The first installing step of the inventive method may include the step of interconnecting the first and second end portions of the first orthodontic archwire to appliances on opposing upper or lower molars in said patient's mouth, wherein upon said activation the first and second end portions of the orthodontic archwire extend from the appliances in one of a substantially parallel orientation and substantially coplanar orientation relative to the reference plane. Further, upon installation the first and second end portions of the orthodontic archwire may preferably extend in a substantially nonconvergent manner relative to said curved central portion.

Following the first installing step, the method may further comprise the step of first removing the first orthodontic archwire from thee patient's mouth, preferably when the middle and intermediate sections of the first orthodontic archwire have reached a position coincidental with the reference plane, then utilizing an orthodontic finishing wire (e.g. stainless steel). For purposes hereof, the term "orthodontic finishing wire" is utilized to mean a monolithic finishing wire which substantially lies within a flat plane or substantially follows a continuous predetermined curve of spee in a passive state.

As will be appreciated upon further description, a two phase treatment method as described above provides for rapid and effective tooth repositioning. In this regard, the use of relatively stiff archwires in each of the two phases particularly differentiates the inventive method from prior art techniques.

By way of elaboration, the first installing step of the inventive method may comprise the steps of deflecting the middle section of the first orthodontic archwire into an arcuate orientation opposite to and even more extreme than its orientation in a passive state, and interconnecting the deflected middle section to at least one incisor in the patient's mouth (e.g., via ligation to a orthodontic appliance mounted on the tooth). Similarly, the first installing step may also include the steps of deflecting the intermediate sections of the first orthodontic archwire into arcuate orientations opposite to and even more extreme than their orientations in a passive state, and interconnecting each of the deflected intermediate sections to at least one bicuspid in the patient's mouth (e.g., via ligation appliances mounted to each of the teeth). As will be appreciated, such deflection and interconnection serves to apply the desired extrusive/intrusive forces to achieve corrective tooth positioning. More particularly, the first orthodontic archwire may be provided so that upon activation the middle section applies a total force of between about 45 gm to 65 gm per mm deflection to the interconnected incisor(s). Similarly, the intermediate sections may be provided so that upon activation they each apply a total force of between about 45 gm and 65 gm per mm deflection to the interconnected bicuspid(s).

In another aspect, the inventive method may further comprise the use of a plurality of inventive orthodontic archwires having one or more features described above during phase I treatment. For example, a first inventive orthodontic archwire may be utilized which applies extrusive/intrusive tooth positioning forces and one of an expansive and narrowing force upon installation in a patient's mouth. Then, after removal of the first orthodontic archwire, a second inventive orthodontic archwire may be installed/removed prior to the finishing wire utilization step. The second archwire may provide for continued vertical tooth positioning and maintenance of a desired arch width prior to the use of an orthodontic finishing wire(s). In this case, it is preferable to remove the second orthodontic archwire when the middle and intermediate sections have reached a partially deflected state coincidental with the reference plane.

Numerous additional aspects, applications and advantages of the present invention will be apparent to these skilled in the art upon consideration of the further description that follows.

DETAILED DESCRIPTION

Figure 1A:
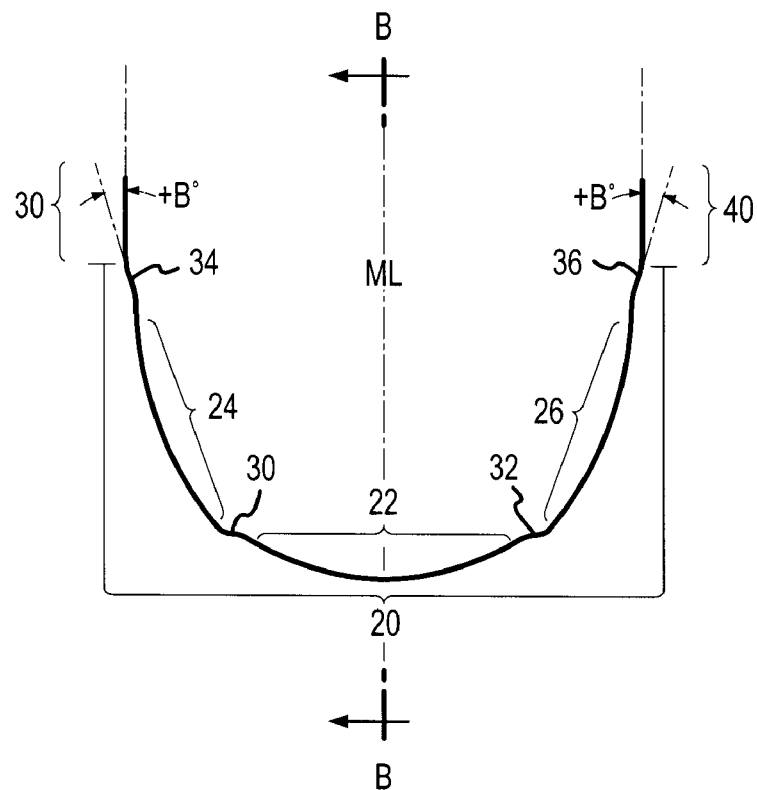
FIG. 1A is a plan view of one embodiment of the present invention in a passive state.
Figure 1B:
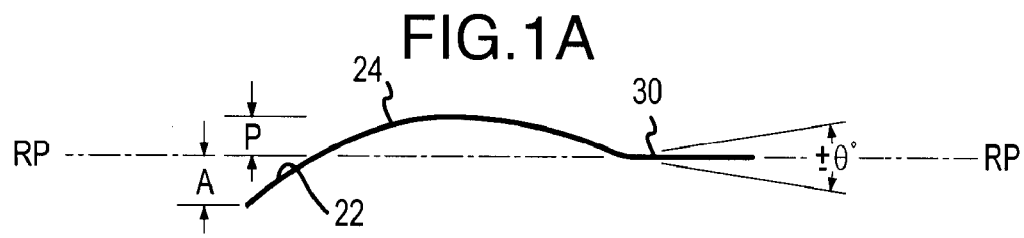
FIG. 1B is an end view of the embodiment of FIG. 1A.
Figure 1C:
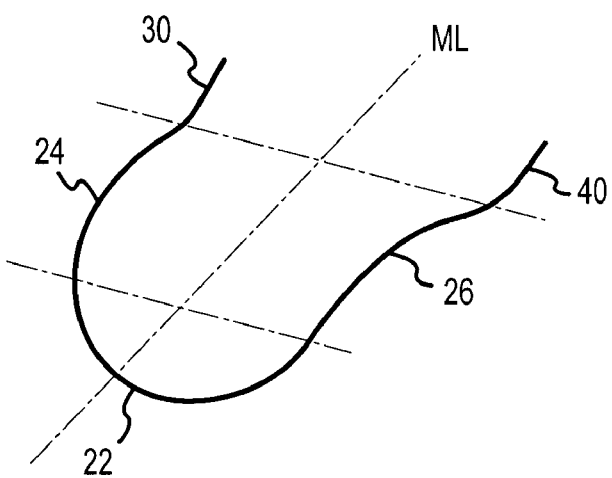
FIG. 1C is an isometric view of the embodiment of FIG. 1A.

FIGS. 1A–1C illustrate different views of one embodiment of the present invention in a passive state.

In particular, a horizontal orthodontic archwire 10 is shown comprising a central curved portion 20 and first and second end portions 30, 40 extending relative to opposing ends of central curved portion 20. The central curved portion 20 includes a middle section 22 and first and second intermediate sections 24, 26 extending relative to opposing ends of middle section 22. Additionally, in the illustrated embodiment, the central curved portion 20 optionally includes step-out segments 30, 32 interposed between the middle section 22 and first and second intermediate sections 24, 26, respectively, and/or step-out segments 34, 36 interposed between the first and second intermediate sections 24, 26 and first and second end portions 30, 40, respectively.

Middle section 22 and intermediate sections 24, 26 are each formed to arcuately project, or vertically bow, one of upwardly or downwardly relative to a horizontal reference plane RP. More particularly, the middle section 22 may be defined to arcuately project one of upwardly and downwardly with respect to the reference plane RP, and the first and second intermediate sections 24, 26 may be defined to arcuately project oppositely to the middle section 22 with respect to the reference plane RP. In the horizontal orthodontic archwire 10 of FIG. 1B the middle section 22 vertically bows downward relative to reference plane RP while the first and second intermediate sections 24, 26 (not shown) vertically bow upward relative to reference plane RP. As will be appreciated, the arcuate middle section 22 and arcuate intermediate sections 24, 26 may be deflected into orientations opposite to and beyond their respective passive state orientations so as to provide for the application of vertically-acting, intrusive/extrusive forces during use of the archwire 10.

To provide for rapid tooth movement, archwire 10 preferably has an ultimate tensile strength of between about 275 KSI and 330 KSI. In this regard, archwire 10 may be fabricated from a single continuous strand of wire, preferably having a round cross-section and diameter of between about 0.012" and 0.022". Further, and by way of example only, archwire 10 may be fabricated from a metal or metal alloy comprising chromium, cobalt, manganese, molybdenum or iron (e.g. a chromium-cobalt alloy). The use of a relatively hard, high-tension metal wire facilitates the provision of a highly activatable, yet mildly contoured appliance.

In the later regard, it is preferable for middle section 22 to have a maximum projection A relative to reference plane RP of between about 0.3 mm and 0.6 mm, in a passive state. Correspondingly, it is preferable for intermediate sections 24, 26 to have a maximum projection P relative to reference plane RP of between about 2 mm and 4 mm in a passive state.

With particular respect to end portions 30 and 40 of the archwire 10 a number of features should be noted. In particular, and as shown in FIG. 1A, it is preferable for end portions 30, 40 to extend from opposing ends of the central curved portion 20 in a non-convergent manner. In this regard, it is preferable for end portions 30, 40 to extend from opposing ends of central curved portion 20 linearly and within an angle range B of between about 0° and +30° relative to an archwire midline ML or axes parallel to ML in a plan or top view. Further, and as best shown in the side view of FIG. 1B, it is preferable for end portions 30, 40 to extend from opposing ends of the central curved portion 20 linearly and within at an angle range θ of between about ±5° relative to the reference plane RP. By way of primary example, the end portions 30, 40 of the archwire 10 shown in FIG. 1B actually lie within the reference plane RP.

Figure 2A:
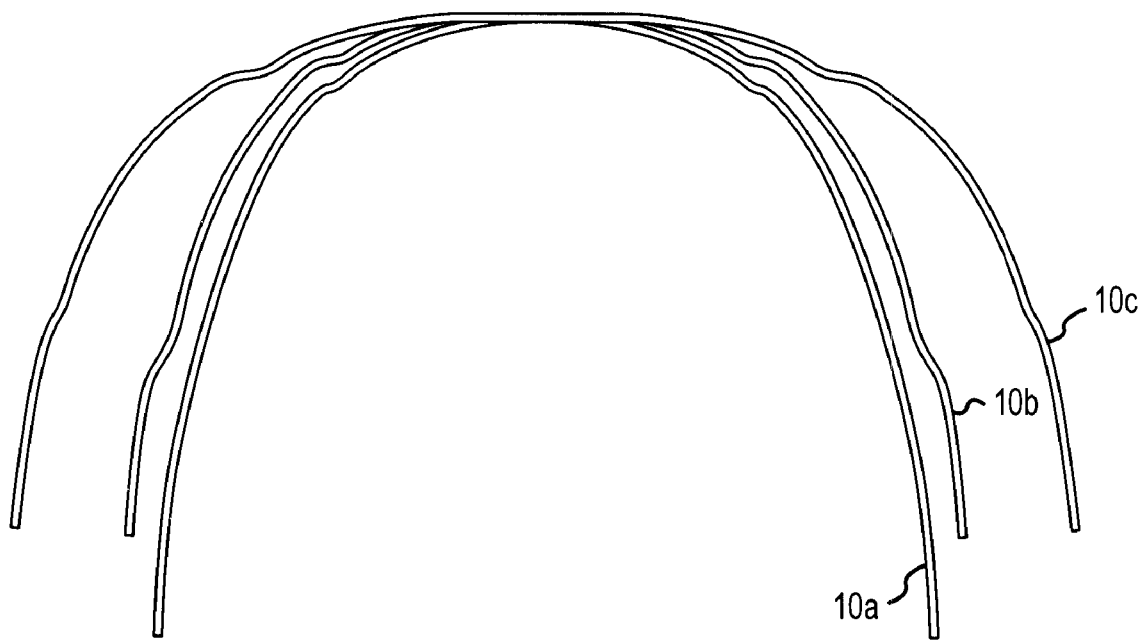
FIG. 2A is a plan view of a set of orthodontic archwire embodiments intended for the maxillary application.
Figure 2B:
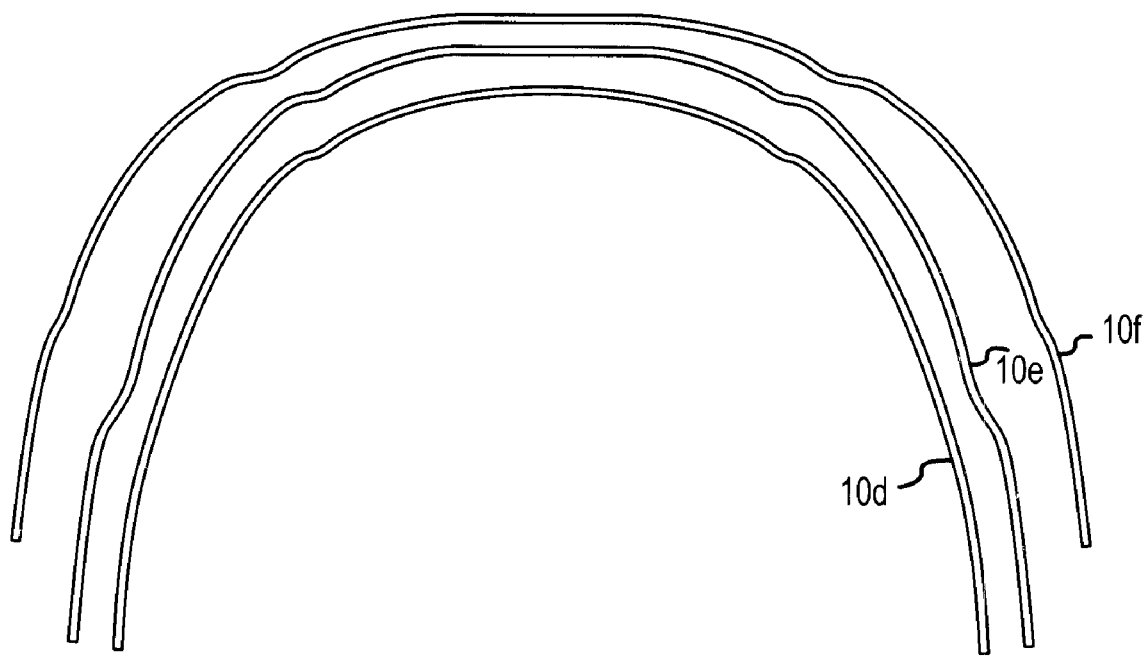
FIG. 2B is a plan view a set of orthodontic archwire embodiments intended for mandibular applications.

FIGS. 2A and 2B illustrate two sets of orthodontic archwires configured as described above, such sets being intended for maxillary and mandibular applications, respectively. More particularly, FIG. 2A shows three orthodontic archwires, 10a, 10b and 10c having increasing cross-widths for differing intended maxillary applications. By way of example, archwire 10a may be selected for use in dechreasing the maxillary inter molar and inter-canine distances of a patient; orthodontic archwire 10b may be selected for use in maintaining the maxillary inter molar and inter-canine distances of a patient; and archwire 10c may be utilized for increasing inter-molar and inter-canine distances of a patient while otherwise providing for the desired bicuspid/incisor intrusion/extrusion. Archwires 10a and 10c, or 10c and 10b, may be successively installed/removed during a phase I treatment regime, followed by the use of a standard phase II orthodontic finishing archwire.

FIG. 2B shows orthodontic archwires 10d, 10e and 10f having increasing cross-widths for differing intended mandibular applications. For example, archwire 10d may be selected for use in decreasing the mandibular inter-molar and inter-canine distances of a patient; orthodontic archwire 10e may be selected for use in maintaining the mandibular inter-molar and inter-canine distances of a patient; and archwire 10f may be utilized for increasing mandibular inter-molar and inter-canine distances of a patient. Archwires 10d and 10e, or 10f and 10e, may be successively installed/removed during a phase I treatment regime, followed by the use of a standard phase II finishing archwire.

Figure 3A:
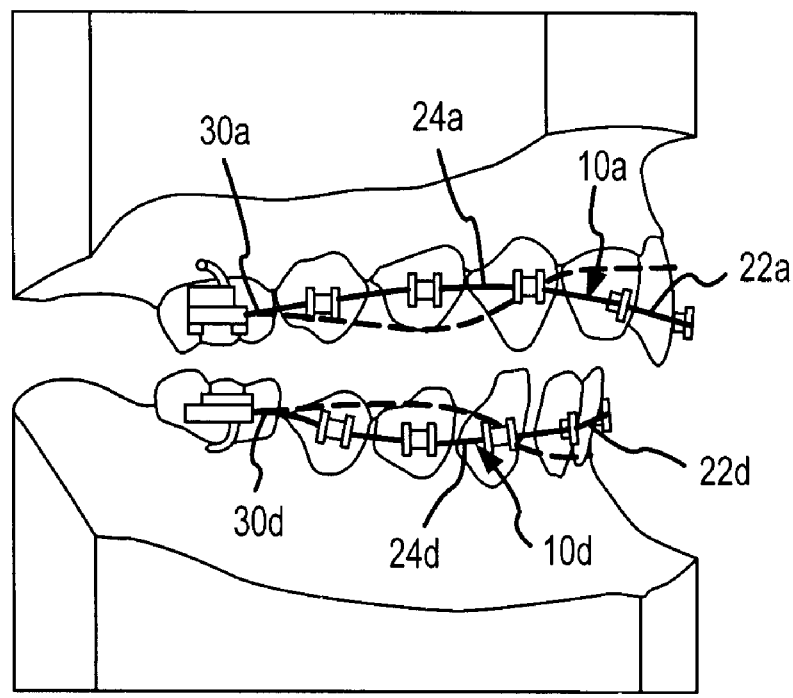
FIG. 3A illustrates the use of orthodontic archwire embodiments on a patient having a Class II malocclusion with impacted bicuspids and over-extruded incisors.
Figure 3B:
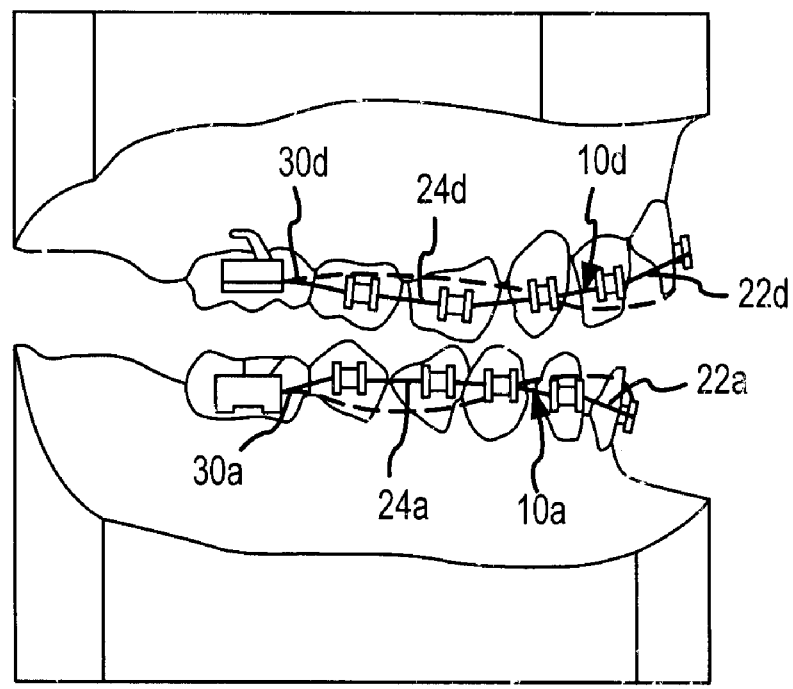
FIG. 3B illustrates the use of orthodontic archwire embodiment for a patient having a Class II malocclusion with over-extruded bicuspids and impacted incisors.

Turning now to FIGS. 3A and 3B two different applications of an exemplary maxillary archwire 10a and an exemplary mandibular archwire 10d are illustrated. In particular, FIG. 3A illustrates an application for addressing a class II malocclusion characterized by a deep anterior over bite and a retrognathic mandible comprising impacted bicuspids and over-extruded incisors.

As illustrated in FIG. 3A, a first end portion 30a of orthodontic archwire 10a is supportably positioned in a buccal tube interconnected to a maxillary first molar. A second end portion 40a (not shown) may be supportably positioned in a buccal tube attached to the opposing maxillary first molar. To activate the archwire 10a from its passive state (as shown by phantom line in FIG. 3A) to the illustrated active state, the archwire 10a may be interconnected (e.g., via ligation) to brackets mounted on the maxillary cuspids, and intermediate sections 24a, 26a (not shown) may be deflected upwardly and interconnected (e.g., via ligation) to brackets mounted on the maxillary first and second bicuspids. Conversely, middle section 22a may be downwardly deflected and interconnected (e.g., via ligation) to brackets mounted on the maxillary central and lateral incisors.

In the mandibular aspect of FIG. 3A, a first end portion 30d of orthodontic archwire 10d is supportably positioned in a buccal tube mounted to a mandibular first molar. Similarly, a second end portion (not shown) may be supportably positioned in a buccal tube mounted to the opposing mandibular first molar. To activate archwire 10d from its passive state (as shown by phantom line in FIG. 3A) to the illustrated active state, the archwire 10d may be interconnected (e.g., via ligation) to brackets interconnected to the maxillary cuspids, and intermediate sections 24d, 26d (not shown) may be deflected downwardly and interconnected (e.g., via ligation) to brackets mounted on the mandibular first and second bicuspids. Conversely, middle section 22d may be upwardly deflected and interconnected (e.g., via ligation) to brackets mounted on the mandibular central and lateral incisors.

After installation, the activated intermediate sections 24a, 26a and 24d, 26d of the orthodontic archwires 10a and 10d shown in FIG. 3A will attempt to return to their passive states, thereby serving to apply corrective positioning forces to extrude the maxillary and mandibular first and second bicuspids. On the other hand, the middle sections 22a and 22d will apply intrusive forces to the maxillary and mandibular central and lateral incisors as they attempt to revert to their passive positions. Further, it should be noted that use of archwires 10a and 10d may also effect maxillary and mandibular arch widening as may be selectively desirable. In this regard, the intrusion of the maxillary/mandibular incisors and/or the widening of the inter-canine distances may act to "unlock" the upper/lower cuspids, thereby facilitating responsive mandibular advancement. Following a desired degree of widening, archwires 10a and/or 10d may be removed and archwires 10b and 10e may be installed to achieve continued bicuspid extrusion/incisor intrusion, while maintaining the desired maxillary and mandibular arch widths.

More generally, it should be noted that regardless of which of the archwires 10a–10c or 10d–10f may be employed in a given application, patient response should be monitored on a periodic basis. More particularly, it is intended that, following installation of any one of the brackets 10a–10c or 10d–10f, such bracket should preferably be removed at the end of phase I treatment when it has assumed an orientation substantially coincidental with its reference plane along its entire length.

Referring now to FIG. 3B, use of exemplary archwires 10a and 10d are shown for addressing a class II malocclusion characterized by an anterior over bite, with impacted incisors and over-extruded bicuspids. As will be appreciated, in this application each of the orthodontic archwires 10a and 10d have been installed "upside down" relative to their installation orientations shown in FIG. 3A. As such, intermediate sections 24b, 26a and intermediate sections 24b, 26d may be activated from a passive state (as shown by phantom lines in FIG. 3B) to an interconnected position with the maxillary and mandibular bicuspids so as to apply intrusive corrective tooth positioning forces thereto. Further, middle sections 22a and 22d may be deflected to an activated state so as to apply extrusive corrective forces to the upper and lower incisors.

As may be appreciated from the foregoing description, the mechanical functioning of the inventive archwire 10 may be considered in terms of four zones: an anterior active zone in which the middle section 22 are interconnected to central and lateral incisors, a cuspid support zone in which first step out segments 30, 32 are interconnected with opposing cuspids, a bicuspid active zone in which the intermediate sections 24, 26 are interconnected to opposing bicuspids and a distal support and molar zone in which the distal end portions 30, 40 are interconnected with the opposing first molars. The anterior active zone provides for the application of intrusive/extrusive forces to the incisors while the bicuspid active zone oppositely provides for extrusive/intrusive forces to the bicuspids. The cuspid support zone provides for a neutral transition between the two active zones. In this regard, it should be noted that since the cuspid is a long-rooted, well anchored tooth, it essentially acts as a hinge-pin or fulcrum, thereby allowing the middle section 22 and intermediate sections 24, 26 to be loaded as a beam in conjunction with the operation of the inventive archwire.

As previously noted, the inventive archwire 10 is installed so that the upward and/or downwardly disposed arcuate middle section 22 and intermediate sections 24, 26 are deflected into opposite orientations. In this regard, the inventive archwire 10 may be characterized as following a sine-wave configuration in a passive state, wherein the upward and downward arcuate sections of the archwire 10 selected for a given patient are 180° out of phase in a passive state with the intruded/extruded teeth comprising the malocclusion to be treated. As such, upon installation the selected archwire 10 will be deflected to an in-phase condition with the corresponding malocclusion and thereby be activated to apply the desired intrusive/extrusive forces appropriate for the situation. Due to the stiffness of the inventive archwire 10, the intrusive/extrusive forces applied in use are sufficient to achieve rapid desired positioning of the bicuspids and incisors. In this regard, in a typical application the progress of incisor and bicuspid tooth movement is monitored, and when the inventive archwire has assumed a position in which the middle section 22 and intermediate sections 24, 26 lie substantially within the reference plane RP (i.e., the two sections are 90° out of phase with the original malocclusion being treated), the archwire is removed from the patient's mouth.

The foregoing description is not intended to limit the scope of the present invention. Additional embodiments, modifications and extensions will be apparent to those skilled in the art and are intended to fall within the scope of the claims which follow.

What is claimed is:

1. An orthodontic archwire, wherein in a passive state said orthodontic archwire is configured to comprise:

a central curved portion and first and second end portions extending from opposing ends of said central curved portion, said central curved portion having a middle section and first and second intermediate sections extending from opposing ends of said middle section, wherein said middle section arcuately projects one of upwardly and downwardly with respect to a reference plane and said first and second intermediate sections arcuately project oppositely to said middle section with respect to said reference plane, and wherein said orthodontic archwire has an ultimate tensile strength of at least about 275 KSI.

2. An orthodontic archwire as recited in claim 1, wherein said first and second end portions extend relative to such opposing ends of the central curved portion within an angle of about 0° to 30° in plan view.

3. An orthodontic archwire as recited in claim 1, wherein said first and second end portions extend relative to said opposing ends of said central curved portion within an angle of about ±5° relative to said reference plane.

4. An orthodontic archwire as recited in claim 1, wherein said first and second end portions extend relative to said opposing ends of said central curved portion in one of a substantially parallel and co-planar orientation relative to said reference plane.

5. An orthodontic archwire as recited in claim 4, wherein said first and second end portion extend substantially linearly relative to such opposing ends of said central curved portion.

6. An orthodontic archwire as recited in claim 1, wherein said arcuate middle section has a maximum projection of between about 0.3 mm and 0.6 mm relative to said reference plane.

7. An orthodontic archwire as recited in claim 5, wherein each of said arcuate first and second intermediate sections have a maximum projection of between 2 mm and 4 mm relative to said reference plane.

8. An orthodontic archwire as recited in claim 7, wherein said arcuate middle section has a maximum projection point of about 0.3 mm and 0.6 mm relative to said reference plane, and wherein each of said arcuate first and second intermediate sections each have a maximum projection of between 2 mm and 4 mm relative to said reference plane.

9. An orthodontic archwire as recited in claim 1, wherein said central curved portion further comprises:
   first and second anterior step-out sections interposed between said middle section and said first and second intermediate sections, respectively.

10. An orthodontic archwire as recited claim 9, wherein said central curved portions further comprises:
    first and second posterior step-out segments adjoining said central curved portion to said first and second end portions, respectively.

11. An orthodontic archwire as recited in claim 1, wherein said orthodontic archwire has a round cross-section with a diameter of between about 0.012" to 0.022".

12. An orthodontic archwire as recited in claim 11, wherein said orthodontic archwire has an ultimate tensile strength of at least about 310 KSI.

13. An orthodontic archwire as recited in claim 12, wherein said first and second end portions extend non-convergently relative to said opposing ends of said central curved portion.

14. An orthodontic archwire as recited in claim 13, wherein said central curved portion further comprises:
    first and second anterior step-out segments interposed between said middle section and said first and second intermediate sections, respectively.

15. An orthodontic archwire as recited in claim 13, wherein said arcuate middle section has a maximum projection of between about 0.3 mm and 0.6 mm relative to said reference plane, and wherein each of said first and second intermediate sections have a maximum projection of between about 2 mm and 4 mm relative to said reference plane.

16. An orthodontic archwire as recited in claim 11, wherein said orthodontic archwire comprises a chromium-cobalt alloy.

17. An orthodontic archwire as recited in claim 1, wherein said orthodontic archwire has a round cross-section with a diameter of between about 0.012" to 0.022", and wherein said orthodontic archwire has an ultimate tensile strength of at least about 275 KSI.

18. An orthodontic archwire as recited in claim 17, wherein said orthodontic archwire comprises a chromium-cobalt alloy.

19. An orthodontic archwire as recited in claim 18, wherein said first and second end portions extend relative to said opposing ends of said central curved portion in one of a substantially parallel and co-planar orientation relative to said reference plane.

20. An orthodontic archwire as recited in claim 18, wherein said horizontal orthodontic archwire has a round cross-section with a diameter of between about 0.01" to 0.022", and wherein said horizontal orthodontic archwire has an ultimate tensile strength of at least about 275 KSI.

21. An orthodontic archwire as recited in claim 20, wherein said orthodontic archwire comprises a chromium-cobalt alloy.

22. An orthodontic archwire, wherein in a passive state said orthodontic archwire is configured to comprise:
    a central curved portion and first and second end portions extending from opposing ends of said central curved portion in one of a parallel and coplanar orientation relative to a reference plane, said central curved portion having a middle section and first and second intermediate sections extending from opposing ends of said middle section, wherein said middle section arcuately projects one of upwardly and downwardly with respect to said reference plane and said first and second intermediate sections arcuately project oppositely to said middle section with respect to said reference plane, and wherein said archwire has an ultimate tensile strength of at least about 275 KSI.

23. An orthodontic archwire as recited in claim 22, wherein said orthodontic archwire has a round cross-section with a diameter of between about 0.012" to 0.022".

24. An orthodontic archwire as recited in claim 23, wherein said ortontic archwire comprises a chromium-cobalt alloy.

25. A method for use of a plurality of orthodontic archwires, comprising:
    first installing a first orthodontic archwire in a patient's mouth, wherein said first orthodontic archwire is deflected from a passive state to an activated state, and wherein in a passive state said first orthodontic arch wire comprises:
    a central curved portion and first and second end portions extending relative to opposing ends of said central curved portion, said central curved portion having a middle section and first and second intermediate sections extending from opposing ends of said middle section, wherein said middle section arcuately projects one of upwardly and downwardly with respect to a reference plane and said first and second intermediate sections arcuately project oppositely to said middle section with respect to said reference plane, and wherein said first orthodontic archwire has an ultimate tensile strength of at least about 275 KSI;

first removing said first orthodontic archwire from said patient's mouth; and, utilizing an orthodontic finishing wire in said patient's mouth after said first installing and first removing steps.

26. A method as recited in claim 25, wherein said first installing step includes:

deflecting said middle section into an arcuate orientation opposite from its arcuate orientation in said passive state and interconnecting said deflected middle section to at least one incisor in said patent's mouth.

27. A method as recited in claim 25, wherein said first orthodontic archwire applies one of an expansive and narrowing force upon installation in a patient's mouth, and wherein said method further comprises:

second installing a second orthodontic archwire in a patient's mouth after said first installing and first removing steps, wherein said second orthodontic archwire is deflected from a passive state to an activated state, and wherein in a passive state said second orthodontic archwire comprises:

a central curved portion and first and second end portions extending from opposing ends of said central curved portion, said central curved portion having a middle section and first and second intermediate sections extending from opposing ends of said middle section, wherein said middle section arcuately projects one of upwardly and downwardly with respect to a reference plane and said first and second intermediate sections arcuately project oppositely to said middle section with respect to the said reference plane, and wherein said second orthodontic archwire has an ultimate tensile strength of at least about 275 KSI; and, second removing and second orthodontic archwire from said patient's mouth prior to said utilizing step.

28. A method as recited in claim 25, said first installing step including:

interconnecting said first and second end portions of appliance on opposing molars in said patient's mouth, wherein upon said activation said first and second end portions of said orthodontic archwire extend from said appliances in one of a parallel orientation and coplanar orientation relative to said reference plane.

29. An orthodontic archwire, wherein in a passive state said orthodontic archwire is configured to comprise:

a central curved portion and first and second end portions extending from opposing ends of said central curved portion, said central curved portion having a middle section and first and second intermediate sections extending from opposing ends of said middle section, wherein said middle section arcuately projects one of upwardly and downwardly with respect to a reference plane and said first and second intermediate sections arcuately project oppositely to said middle section with respect to said reference plane, and wherein said central curved portion further comprises first and second anterior step-out sections interposed between said middle section and said first and second intermediate sections, respectively.

30. An orthodontic archwire as recited in claim 29, wherein said first and second end portions extend relative to said opposing ends of said central curved portion within an angle of about ±5° relative to said reference plane.

31. An orthodontic archwire as recited in claim 29, wherein said first and second end portions extend relative to said opposing ends of said central curved portion in one of a substantially parallel and co-planar orientation relative to said reference plane.

32. An orthodontic archwire as recited in claim 31, wherein said central curved portions further comprises:

first and second posterior step-out segments adjoining said central curved portion to said first and second end portions, respectively.

33. An orthodontic archwire, wherein in a passive state said orthodontic archwire is configured to comprise:

a central curved portion and first and second end portions extending from opposing ends of said central curved portion, said central curved portion having a middle section and first and second intermediate sections extending from opposing ends of said middle section, wherein said middle section arcuately projects one of upwardly and downwardly with respect to a reference plane and said first and second intermediate sections arcuately project oppositely to said middle section with respect to said reference plane, and wherein said first and second end portions extend relative to said opposing ends of said central curved portion within an angle of about ±5° relative to said reference plane.

34. An orthodontic archwire as recited in claim 33, wherein said central curved portion further comprises:

first and second anterior step-out sections interposed between said middle section and said first and second intermediate sections, respectively.

35. An orthodontic archwire as recited in claim 34, wherein said central curved portions further comprises:

first and second posterior step-out segments adjoining said central curved portion to said first and second end portions, respectively.

* * * * *

UNITED STATES PATENT AND TRADEMARK OFFICE
CERTIFICATE OF CORRECTION

PATENT NO. : 6,431,861 B1
DATED : August 13, 2002
INVENTOR(S) : White

It is certified that error appears in the above-identified patent and that said Letters Patent is hereby corrected as shown below:

Column 3,
Line 44, delete "stiffniess", and insert therefor -- stiffness --;

Column 6,
Lines 39-40, delete "dechreasing", and insert therefor -- decreasing --;

Column 10,
Line 24, delete "0.01"", and insert therefor -- 0.012" --;
Line 49, delete "ortontic", and insert therefor -- orthodontic --.

Signed and Sealed this

Twenty-first Day of January, 2003

JAMES E. ROGAN
*Director of the United States Patent and Trademark Office*